US009492601B2

(12) United States Patent
Casas et al.

(10) Patent No.: US 9,492,601 B2
(45) Date of Patent: Nov. 15, 2016

(54) SUCTION DETECTION ON AN AXIAL BLOOD PUMP USING BEMF DATA

(71) Applicant: HeartWare, Inc., Miami Lakes, FL (US)

(72) Inventors: Fernando Casas, Miami Lakes, FL (US); Carlos Reyes, Pembroke Pines, FL (US)

(73) Assignee: HeartWare, Inc., Miami Lakes, FL (US)

( * ) Notice: Subject to any disclaimer, the term of this patent is extended or adjusted under 35 U.S.C. 154(b) by 457 days.

(21) Appl. No.: 13/951,302

(22) Filed: Jul. 25, 2013

(65) Prior Publication Data

US 2014/0100413 A1 Apr. 10, 2014

Related U.S. Application Data

(63) Continuation-in-part of application No. 13/355,297, filed on Jan. 20, 2012.

(60) Provisional application No. 61/831,027, filed on Jun. 4, 2013, provisional application No. 61/434,894, filed on Jan. 21, 2011.

(51) Int. Cl.
*A61M 1/12* (2006.01)
*A61M 1/10* (2006.01)

(52) U.S. Cl.
CPC ............. *A61M 1/127* (2013.01); *A61M 1/101* (2013.01); *A61M 1/1015* (2014.02); *A61M 1/1086* (2013.01); *A61M 1/122* (2014.02)

(58) Field of Classification Search
CPC ................................ A61M 1/127; A61M 1/12

USPC ........................................... 606/16; 623/3.28
See application file for complete search history.

(56) References Cited

U.S. PATENT DOCUMENTS

| | | | |
|---|---|---|---|
| 6,066,086 A | 5/2000 | Antaki et al. | |
| 6,605,032 B2 | 8/2003 | Benkowski et al. | |
| 7,166,980 B1 | 1/2007 | LeGrand | |
| 7,497,116 B2 | 3/2009 | Miyakoshi | |
| 7,951,062 B2 | 5/2011 | Morello | |
| 2003/0069465 A1 | 4/2003 | Benkowski et al. | |
| 2004/0215050 A1 | 10/2004 | Morello | |

(Continued)

OTHER PUBLICATIONS

Partial Inernational Search Report for Application No. PCT/US2014/040847 dated Oct. 9, 2014.

(Continued)

*Primary Examiner* — Matthew Schall
(74) *Attorney, Agent, or Firm* — Lerner, David, Littenberg, Krumholz & Mentlik, LLP

(57) ABSTRACT

The presence or absence of a suction condition in an implantable blood pump is determined at least in part based on a parameter related to flow, such as a parameter related to thrust on the rotor of the pump. A local extreme of the parameter representing the minimum flow during ventricular diastole in an earlier interval is used to establish a threshold value. A value of the parameter representing the minimum flow during ventricular diastole in a later interval is compared to this threshold. If the comparison indicates a substantial decline in the minimum flow between the earlier and later intervals is associated with a suction condition. During the absence of a suction condition, the threshold is continually updated, so that the system does not indicate presence of a suction condition if the flow decreases gradually.

28 Claims, 15 Drawing Sheets

(56) References Cited

U.S. PATENT DOCUMENTS

| | | |
|---|---|---|
| 2006/0229488 A1 | 10/2006 | Ayre et al. |
| 2007/0100196 A1 | 5/2007 | LaRose et al. |
| 2007/0232934 A1 | 10/2007 | LaRose et al. |
| 2007/0282298 A1 | 12/2007 | Mason |
| 2008/0281146 A1 | 11/2008 | Morello |
| 2010/0185280 A1 | 7/2010 | Ayre et al. |
| 2012/0245681 A1 | 9/2012 | Casas |
| 2013/0046129 A1 | 2/2013 | Medvedev et al. |

OTHER PUBLICATIONS

International Search Report and Written Opinion for Application No. PCT/US2014/040847 dated May 27, 2015.

International Search Report issued by the International Searching Authority (ISA/US) on May 23, 2012 in connection with International Application No. PCT/US2012/022096.

Written Opinion of the International Searching Authority issued by the International Searching Authority (ISA/US) on May 12, 2012 in connection with International Application No. PCT/US2012/022096.

Office Action issued Mar. 27, 2013 in connection with U.S. Appl. No. 13/355,297.

Notification Concerning Transmittal of International Preliminary Report on Patentability (Chapter I of the Patent Cooperation Treaty), including International Preliminary Report on Patentability and Written Opinion of the International Searching Authority, mailed Aug. 1, 2013 by the International Bureau of WIPO in connection with PCT International Application No. PCT/US2012/022096, filed Jan. 20, 2012.

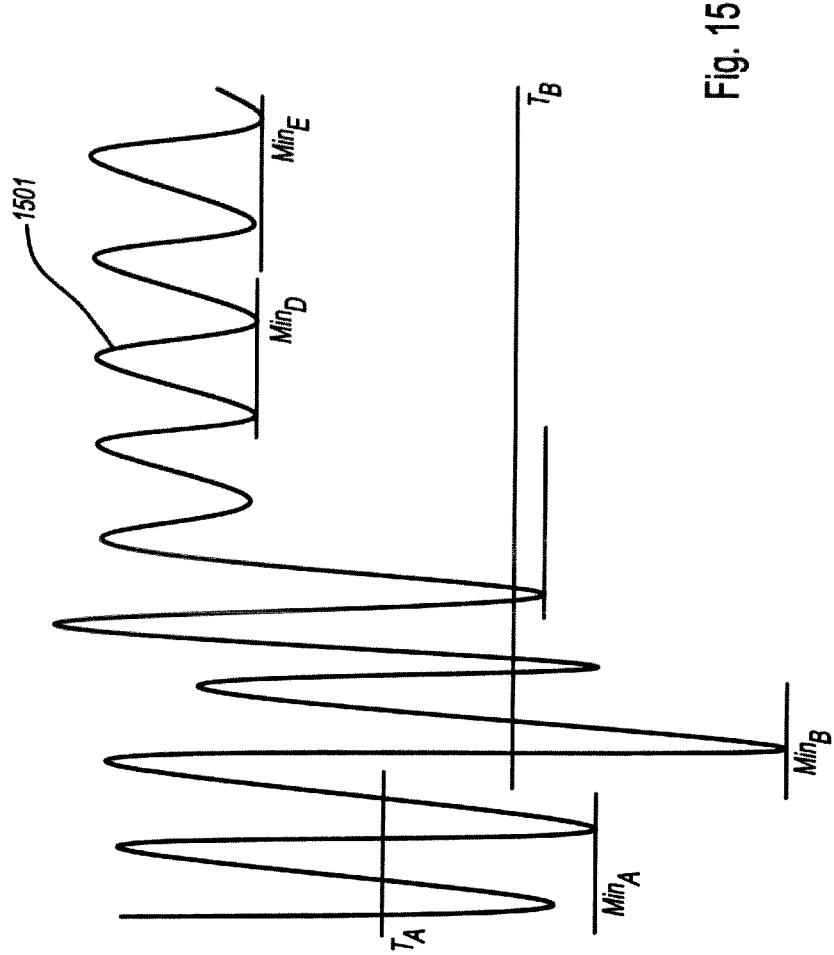

SUCTION DETECTION ON AN AXIAL BLOOD PUMP USING BEMF DATA

CROSS-REFERENCE TO RELATED APPLICATIONS

The present application is a continuation-in-part of U.S. patent application Ser. No. 13/355,297, filed Jan. 20, 2012, which claims the benefit of priority to U.S. Provisional Patent Application No. 61/434,894 filed Jan. 21, 2011, the disclosures of which are hereby incorporated herein by reference.

FIELD OF THE INVENTION

The present invention relates to blood pumps, to methods of using blood pumps, and to control circuits adapted for use with blood pumps.

BACKGROUND OF THE INVENTION

Implantable blood pumps may be used to provide assistance to patients with late stage heart disease. Blood pumps operate by receiving blood from a patient's vascular system and impelling the blood back into the patient's vascular system. By adding momentum and pressure to the patient's blood flow, blood pumps may augment or replace the pumping action of the heart. For example, a blood pump may be configured as ventricular assist device or "VAD." Where a VAD is used to assist the pumping action of the left ventricle, the device draws blood from the left ventricle of the heart and discharges the blood into the aorta.

To provide clinically useful assistance to the heart, blood pumps must impel blood at a substantial blood flow rate. For an adult human patient, a ventricular assist device may be arranged to pump blood at about 1-10 liters per minute at a pressure differential across the pump of about 10-110 mm Hg, depending on the needs of the patient. The needs of the patient may vary with age, height, and other factors.

It is desirable to monitor the rate at which blood is impelled by a blood pump. For example, if a VAD is operated at a flow rate in excess of the inflow rate of blood to the ventricle, the VAD will create a suction condition within the ventricle, wherein the ventricle is collapsed and essentially devoid of blood. This condition is undesirable. In this condition, the flow rate through the pump will decline rapidly. Likewise, if the intake or outlet of the pump is occluded, the flow rate will decline gradually. If the flow rate through the pump declines, either rapidly (e.g., as a result of suction condition) or gradually (e.g., as a result of an obstruction or occlusion) to the extent that the flow rate is insufficient, the device will not provide sufficient circulatory assistance to the patient. Excessive flow also can create undesirable conditions. Therefore, it would be desirable to provide a blood pump controller which can monitor the blood flow rate produced by the blood pump which it controls.

Further, when monitoring the blood flow rate, it is desirable to identify whether a decline in flow rate is the effect of a suction condition or the effect of an occlusion. Although both suction and occlusion conditions result in a decline in blood flow rate, these conditions are generally treated differently in order to overcome each respective condition. Moreover, it is often undesirable to treat an occlusion in the same manner as a suction condition would be treated. It is likewise undesirable to treat a suction condition in the same manner as an occlusion would be treated. Therefore, it is desirable to provide a blood pump controller that is capable of differentiating between a blood flow decline caused by a suction condition and a blood flow decline caused by an occlusion.

BRIEF SUMMARY OF THE INVENTION

One aspect of the invention provides an implantable blood pump system. The system according to this aspect of the invention desirably comprises a pump and a control circuit. The pump includes a housing having an axis, and a rotor disposed within the housing, the rotor being rotatable around the axis. The control circuit is operatively coupled to the pump and configured to determine a parameter related to thrust on the rotor along the axis, and to determine a flow rate of blood based at least in part on the parameter. The control circuit may be arranged to control operation of the pump based at least in part on the determined flow rate. The parameter related to thrust may be the back electromotive force generated in a coil or coils of the pump stator.

In another aspect, a control circuit is provided for controlling the operation of a blood pump. The control circuit according to this aspect of the invention desirably comprises a parameter determination circuit and a flow rate determination circuit. The parameter determination circuit desirably is operative to determine a parameter related to thrust generated by a rotor of the pump. The flow rate determination circuit is operative to determine a flow rate of blood based at least in part on the parameter. The pump driver circuit may also be operative to control the pump based on the determined flow rate.

In yet another aspect of the invention, a method is provided for controlling an implantable blood pump. The method desirably comprises determining a parameter relating to thrust generated by a rotor of the pump, and determining a flow rate of blood through the pump, wherein the flow rate is determined based on the parameter and speed of rotation of a rotor of the pump. The method may also include controlling the operation of the pump based on the determined flow rate.

In yet a further aspect of the invention, a control circuit is provided for monitoring the operation of an implantable blood pump. The control circuit desirably comprises a threshold value determination circuit operative to repeatedly determine a threshold value of a parameter related to thrust along an axis of a rotor of the pump based on values of the parameter occurring during a period of time prior to each determination. The control circuit may also include a comparison circuit operative to compare one or more values of the parameter with the threshold value from the last previous determination. The control circuit may further include a condition determination circuit operative to determine the presence or absence of one of a suction condition and a suction clearance condition based at least in part on the result yielded by the comparison circuit.

Another aspect of the invention provides for an implantable blood pump system. The system desirably comprises a pump including a housing having an axis, and a rotor disposed within the housing, the rotor being rotatable around the axis, and the above described control circuit operatively coupled to the pump.

In yet another aspect of the invention, a control circuit is provided for monitoring the operation of an implantable blood pump operatively coupled to the control circuit. The control circuit desirably comprises a drive circuit operative to repeatedly reduce the speed of the pump from a starting speed to one of a first and second reduced speed, the first reduced speed being faster than the second reduced speed, and to increase the speed of the pump from the one of the first and second reduced speeds to the starting speed. The rate of increasing the speed of the pump may be more gradual than the rate of reducing the speed of the pump. The repeated reduction of the pump speed may alternate between the first and second reduced speeds.

Yet a further aspect of the invention provides for another implantable blood pump system. This system desirably comprises a pump including a housing having an axis, and a rotor disposed within the housing, the rotor being rotatable around the axis. The stator may incorporate a plurality of coils for applying a rotating magnetic field to the rotor. The system may further include a control circuit operatively coupled to the pump. The control circuit may be configured to determine a threshold value based directly on a measured back electromotive force (BEMF) in one or more of the plurality of coils, and determine the presence or absence of a suction condition based at least in part on the threshold value.

In yet another aspect of the invention, a method is provided for monitoring operation of an implantable blood pump. The method desirably comprises repeatedly determining a threshold value of a parameter related to thrust along an axis of a rotor of the pump based on values of the parameter occurring during a period of time prior to each determination. The method may also include comparing one or more values of the parameter with the threshold value from the last previous determination. The method may further include determining the presence or absence of one of a suction condition and a suction clearance condition based at least in part on the comparison.

BRIEF DESCRIPTION OF THE DRAWINGS

FIG. 15 is graph depicting an embodiment of the method depicted in FIG. 14.

DETAILED DESCRIPTION

Figure 1:
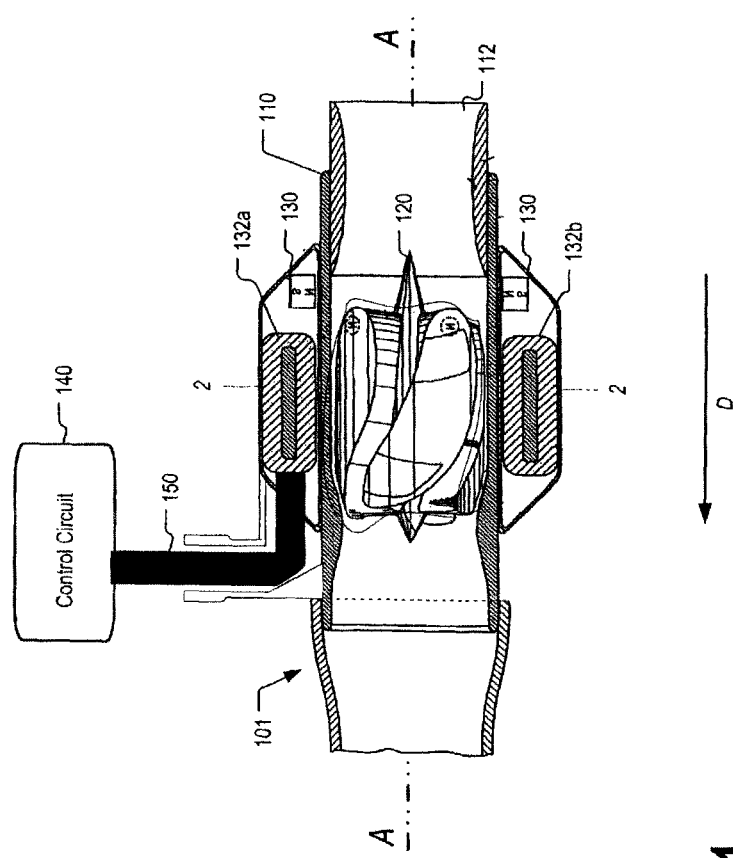
FIG. 1 is a schematic, partially sectional view of a blood pump system in accordance with one embodiment of the invention
Figure 2:
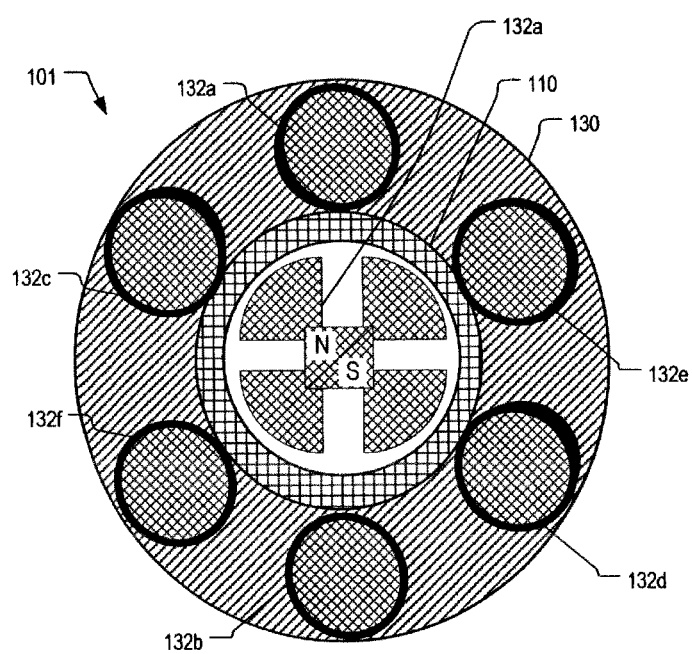
FIG. 2 is a diagrammatic sectional view taken along line 2-2 in FIG. 1.
Figure 3:
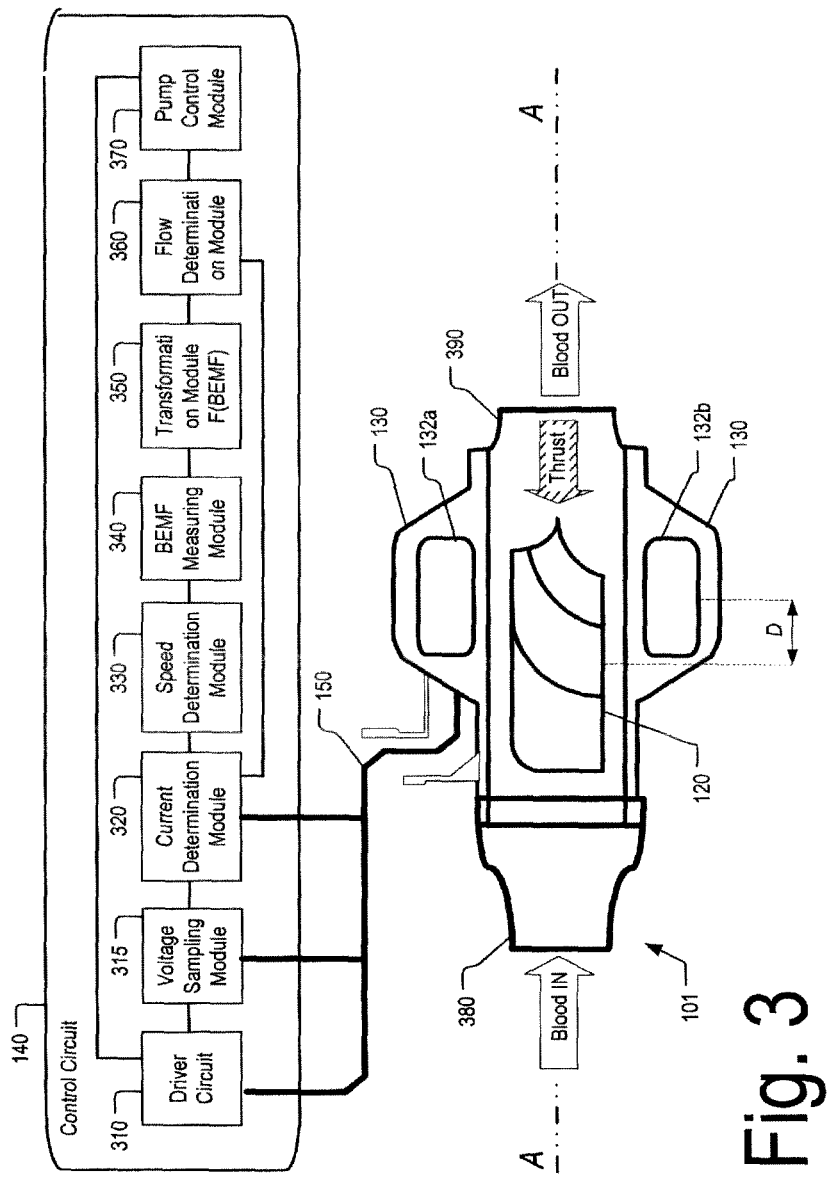
FIG. 3 is a partially functional block diagrammatic, partially sectional view of the blood pump system of FIG. 1.

FIGS. 1-3 depict a blood pump system 100 in accordance with one embodiment of the invention. The blood pump system 100 according to this embodiment includes a control circuit 140 connected via a cable feed 150 to a blood pump 101. The blood pump 101 includes a housing 110 defining a bore 112 having an axis A. A rotor 120 is disposed within the bore. The rotor 120 has a permanent magnetization with flux direction perpendicular to the axis of the bore. The rotor constitutes an impeller configured to push blood in a downstream direction D parallel to the bore 112 when the rotor is turning.

The pump also includes a stator 130. The stator includes coils 132a-e (FIG. 2) connected in a WYE or delta configuration and placed around the circumference of the housing 110. The coils are arranged in pairs diametrically opposed to one another. Thus, coils 132a and 132b form one pair, coils 132c and 132d form another pair, and coils 132e and 132f form another pair. When the coils are driven using a 3-phase current, they provide a magnetic field directed transverse to the bore axis and which rotates around the axis. The magnetic field will interact with the magnetic field of the rotor 120 causing the rotor to turn. In operation, the rotor 120 may be suspended within the bore 112 by magnetic forces, hydrodynamic forces, or both in combination. Desirably, these forces support the rotor so that it does not contact housing 110 during normal operation. Further details about suspended-rotor blood pumps, such as the pump 101, are provided in U.S. Published Patent Application No. 20070100196, entitled "Axial Flow Pump with Multi-Grooved Rotor," disclosure of which is incorporated herein by reference.

The control circuit 140 comprises driver circuit 310, current determination module 320, and speed determination module 330. BEMF measuring module 340, transformation module 350, flow determination module 360, and pump control module 370. The modules are depicted and discussed with reference to their individual functions. One or more of the modules 310-270 may be implemented using software operating in a computer system including a general-purpose or special purpose processor, in digital circuitry, or in using analog circuitry.

The driver circuit 310 is an electrical circuit for powering the pump 101 with a 3-phase current. Each phase of the three-phase current preferably is in the form of a generally rectangular wave including alternating off or "open-phase" periods in which power is not applied by the drive circuit and on or "closed-phase" periods during which power is applied. The periods of the various phases are arranged so that at any moment, two pairs of coils are on or closed-phase and one pair is off or open-phase. The open-phase and closed-phase periods of the various phases are arranged so that the various pairs of coils go to an open-phase state in sequence, thus creating the rotating magnetic field that actuates the rotor. Driver circuit 310 applies pulse width modulation during each on or closed-phase period. Thus, during each on or closed-phased period, the voltage applied to the pair of coils varies repeatedly between zero and a selected maximum value at a pulse modulation or chopping frequency much higher than the frequency of the rectangular waveform of the repeating closed-phase and open-phase period.

Figure 4:
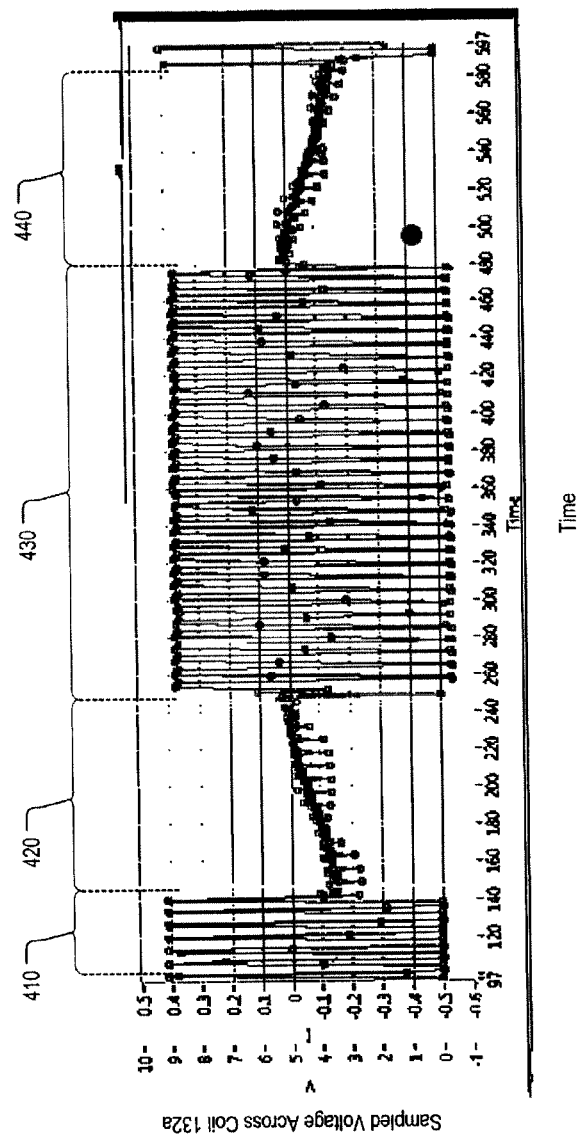
FIG. 4 depicts a plot of voltage sampled across a coil in a stator of the blood pump of FIGS. 1-3.

For example, FIG. 4 depicts the voltage across coil pair 132a and 132b. During each on or closed-phase period 410 and 430, the voltage applied by the drive circuit is repeatedly chopped or pulse-width modulated. During open-phase periods 420 and 440, the coils 132a and 132b are not energized by the driver circuit 310. During the open-phase periods, a relatively small voltage appears across coils 132a and 132b. This voltage is composed primarily of voltage induced in the coil pair 132a and 132b by the rotating magnetic rotor 120. This induced voltage is referred to as the back electromagnetic force of "BEMF." The BEMF varies in a generally sinusoidal manner; the open periods correspond to the zero-crossings of the sinusoidal variation. The voltage appearing on the coil pair during the open periods also includes some higher-frequency components representing voltage induced in pair 132a and 132b by the fluctuating pulse-width modulated currents in the other coil which are in the closed-phase or on state. During the open periods 420 and 440, the voltage across coil pair 132a and 132b is less than a given threshold (e.g., +/−0.5V).

Returning to FIG. 3, the current determination module 320 may include hardware and/or software for determining the amount of current supplied to the pump 101. For example, the current determination module may include a known resistance in series with coil pair 132a and 132b, and an analog-to-digital converter arranged to sample the voltage across the known resistance so that each such sample represents the instantaneous current passing through the coil pair, as well as an averaging circuit arranged to average these sample to provide a measure of the average current passing through the coil pair.

The control circuit further includes a voltage sampling circuit 315. The voltage-sampling circuit may include an analog-to-digital converter connected across coil pair 132a and 132b and arranged to capture successive samples of the voltage appearing across the coil pair. The voltage-sampling circuit may also include a digital filter for suppressing variations in the sampled voltage at frequencies at or above the pulse-width modulation or chopping frequency used by the drive circuit, so as to provide a filtered series of values. Alternatively, the sampling circuit may include an analog low-pass filter connected between the analog-to-digital converter and the coil pair.

A speed determination module 330 is operatively connected to the sampling circuit 315 to receive the filtered values from sampling circuit. The speed determination module is arranged to deduce the speed of rotation of the magnetic field, and hence the speed of rotation of rotor 120, from these values. For example, the speed determination module may be arranged to record the time when the voltage on coil pair 132a and 132b drops below the threshold value associated with the open-phase periods as the beginning of an open-phase period, and to calculate the interval between the beginnings of successive open-phase periods. The speed of rotation is inversely proportional to this time.

The BEMF measuring module 340 is also connected to receive the stream of sampled voltage values from sampling circuit 315, and to record the filtered voltage values during the open-phase periods. These filtered values represent the BEMF generated by the pump. Transformation module 350 is connected to BEMF measuring module 340. The transformation module processes the data collected by the BEMF measuring module 340 to determine a value of a function of the BEMF. The function is referred to herein as F(BEMF). F(BEMF) may be rate of change of the BEMF with respect to time during each open-phase period, i.e., the absolute value of the slope of the BEMF versus time. Like the BEMF measuring module 340, the transformation module 350 may also be implemented using hardware and/or software.

The flow determination module 360 may include hardware and/or software for determining the rate at which blood is impelled by the pump 101. The flow determination module is operatively connected to current determination module 320, speed determination module 330 and transformation module 350 so that the flow determination module 360 receives values representing current, speed and F(BEMF). The flow determination module is arranged to determine the flow rate from the pump based on this information as further discussed below. Pump control module 370 is operatively linked to flow determination module 360 so that the pump control module 370 receives values representing the flow rate from the flow determination module. The pump control module is also linked to driver circuit 310. The pump control module is arranged to determine a desired pump speed based, at least in part, on the flow rate and to command driver circuit 310 accordingly. Thus, the pump control module can control the pump 100 based on the blood flow rate determined by the flow determination module 370 as further discussed below.

In operation, the control circuit 140 powers the pump 101, via the driver circuit 310, thereby causing the rotor 120 to spin. As the rotor 120 spins, blood enters the pump 101 through the inflow end 380 after which the blood is impelled by the rotor 120 from the outflow end 390. As the blood passes through the pump 101, it imparts a thrust on the rotor 120. The magnitude of this thrust is related to the flow rate of blood through the pump.

As discussed above, the rotor 120 is held in position by magnetic and hydrodynamic forces. However, these forces do not hold the rotor with infinite rigidity. Therefore, thrust imparted to the rotor 120 causes the rotor 120 to move by a displacement distance D towards the inflow end 380. For at least some range of thrust values, distance D is related to the magnitude of the thrust and, thus, related to the blood flow rate. Distance D is greatly exaggerated in FIG. 3 for clarity of illustration; in practice, distance D is small in comparison to the dimension of the rotor and pump. Axial displacement of rotor 120 also changes the alignment between the rotor and the coils 132 of the pump. This alters the magnetic interaction between the rotor and the coils of the stator, and thus alters the BEMF. The effect of this alteration will depend, inter alia, on the alignment between the rotor and the coils under zero-thrust conditions and on the configuration of the rotor and the coils. However, for any particular pump operating at a particular speed with blood of a particular viscosity, the effect is repeatable and predictable. The relationship between BEMF and flow rate at one pump speed and blood viscosity for the pump of FIGS. 1-3 is shown by curve 620 in FIG. 6. In the particular embodiment of FIGS. 1-3, the BEMF increases with increasing blood flow rate at least in the range between zero and a flow rate T. Although the present invention is not limited by any theory of operation, it is believed the thrust on the rotor is a composite of reaction components directed upstream toward the inlet end of the pump and viscous components directed downstream toward the outlet end. At zero flow, the reaction components predominate and thus the thrust is directed upstream. As the flow rate increases from zero, the viscous components increase and thus the magnitude of the thrust decreases. As the thrust decreases, distance D decreases and the rotor moves into better alignment with the coils, so that BEMF increases.

Figure 6:
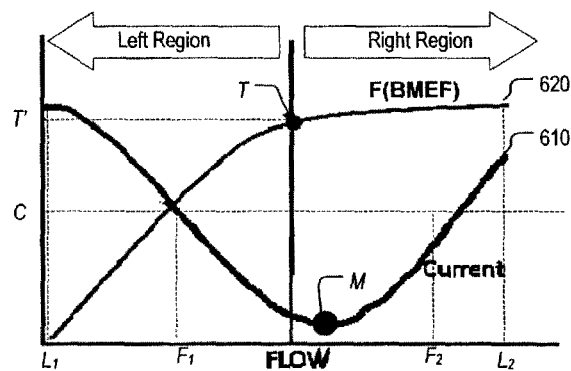
FIG. 6 is a graph depicting certain relationships in operation of the blood pump system of FIGS. 1-3.

Because F(BEMF) (the rate of change in BEMF in the open phase period) is proportional to BEMF, the same curve 620 depicts the relationship between F(BEMF) and the blood flow rate. Stated another way. F(BEMF) is a parameter related to the thrust on the rotor. The flow determination module 360 determines the flow rate of blood through the pump based in part on this parameter as further explained below. As also shown in FIG. 6, the current consumed by the pump also varies with flow rate. Curve 610 depicts the variation of current with flow rate at a particular pump operating speed. The flow determination module 360 uses both current and F(BEMF) to determine the flow rate. In brief, the flow determination module uses the value of F(BEMF) and the relationship between F(BEMF) to derive an initial estimate of flow rate. If this initial estimate indicates that the flow rate is below a value M referred to herein as the "fiducial" value, the flow determination module uses the value of current and the relationship between current and flow rate indicated in the left region of curve 610 to determine the flow rate. If the initial estimate of flow rate indicates that the flow rate is above the fiducial value M, the flow determination module uses the value of the current and the relationship between current and flow rate indicated in the right region of curve 610 to determine the flow rate.

Figure 5:
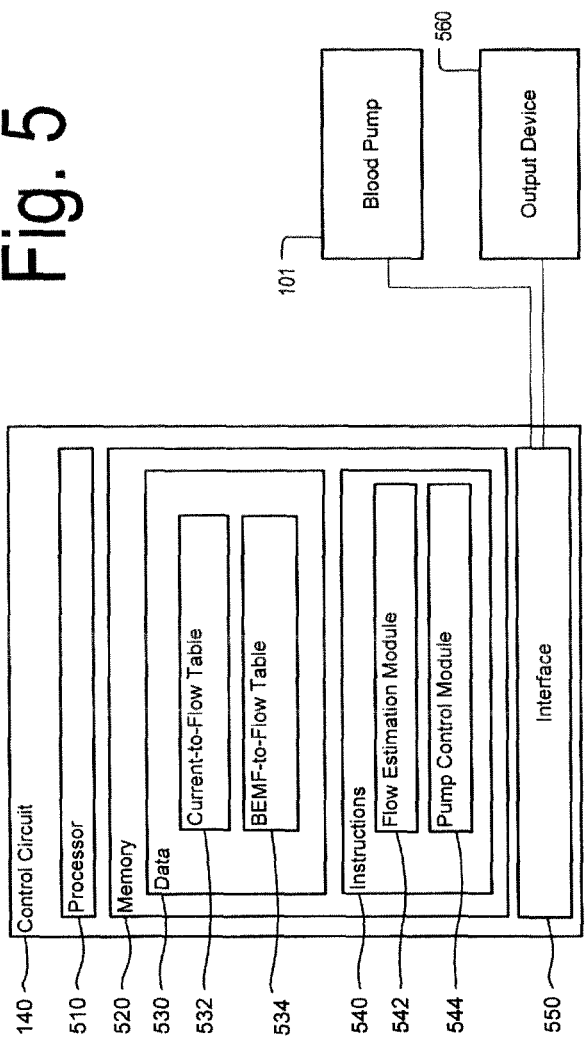
FIG. 5 is a schematic diagram showing the hardware and software used in the blood pump system of FIG. 1-3

The various modules discussed above with reference to FIG. 3 desirably are implemented at least in part by a general-purpose processor which performs functions associated with the various modules. FIG. 5 depicts this implementation. As shown, the control circuit 140 is implemented using a processor 510, a memory 520, data 530, instructions 540, and an interlace 550. Memory 520 stores information accessible by processor 510, including instructions 540 that may be executed by the processor 510. The memory also includes data 530 that may be retrieved, manipulated or stored by the processor. The memory may be of any type capable of storing information accessible by the processor, such as a hard-drive, memory card, ROM, RAM, DVD, CD-ROM, write-capable, and read-only memories. The processor 510 may be any well-known processor, such as commercially available processors. Alternatively, the processor may be a dedicated controller such as an ASIC.

Data 530 may be retrieved, stored or modified by processor 510 in accordance with the instructions 540. The data may also be formatted in any computer-readable format such as, but not limited to, binary values, ASCII or Unicode. Moreover, the data may comprise any information sufficient to identify the relevant information, such as numbers, descriptive text, proprietary codes, pointers, references to data stored in other memories (including other network locations) or information that is used by a function to calculate the relevant data.

A current-to-flow table 532 is a tabular representation of the function 610 depicted in FIG. 6. The current-to-flow table 532 may identify one or more blood flow rates that result when a given amount of current is used to power the pump 101. An example of a current-to flow table 532 is provided as Table 1. As shown in FIG. 6, the relationship 610 between current and flow is not a single-valued function. Curve 610 illustrates, for instance, that when C amperes are used to power the pump 101, the pump 101 may impel blood at either F, L/min or F 2 L/min. In other words, the plot illustrates that in this embodiment, there is a many-to-one mapping between current and blood flow rate. As also shown by curve 610, the relationship is such that for any flow in the left region of the current-to-flow relationship, below the fiducial value M liters/minute, there is a one-to-one mapping between current and flow. At any flow above the fiducial value M liters/minute, there is a different one-to-one mapping between current and flow.

Thus, as depicted in Table 1, the current-to-flow map stores plural values of flow rate for each value of current, one associated with the left region and one associated with the right region. At a value of current corresponding to the fiducial flow rate (1.0 amps in the example of Table I), the two values are the same; the current-to-flow table 532 indicates that when the pump 101 is powered with 1.0 amps of current, it pumps blood at the rate of 2 L/min. At a current of 1.2 amps, the blood flow rate is either 1.5 L/min or 3.0 L/min. The current-to-flow relationship varies with the speed of operation of the pump, i.e., the rotation rate of the rotor. The current-to-flow relationship also varies with viscosity of the blood. The viscosity of the blood is directly related to the hematocrit, i.e., the proportion of the blood volume occupied by red blood cells. Therefore, the current-to-flow table stores different sets of values, each associated with a range a particular pump operating speed and blood viscosity. Each such set of values includes a fiducial value M. Sets of values for other pump operating speeds and viscosities are calculated from the stored sets by interpolation. The flow calculation module selects the appropriate set of values based on the speed of operation of the pump and on a value of hematocrit or blood viscosity for the patient which has been supplied to the system from an external source through interface 550. The current-to-flow table 532 may be implemented as a file, a data structure, as part of a database, or in any other suitable form.

TABLE 1

Current-to-Flow Map

| Current Flow Rate | Blood Flow Rate Left Region | Blood Flow Rate Right Region |
|---|---|---|
| 1.0 amps | 2.0 L/min | 2.0 L/min |
| 1.2 amps | 1.5 L/min | 3.0 L/min |
| 1.4 amps | 1.0 L/min | 4.0 L/min |

F(BEMF)-to-flow table 534 may be a tabular representation of the function 620 depicted In FIG. 6. The F(BEMF)-to-flow table 534 identifies the flow rate of blood impelled by the pump 101 when the F(BEMF) indicates that the BEMF in coil pair 132a and 132b changes at a given rate with respect to time. The BEMF-to-flow relationship also changes with pump operating speed and viscosity, i.e., hematocrit. Therefore, table 534 includes different sets of data, each associated with a given speed of rotation of the rotor 120 and a given viscosity. Here again, values for pump operating speeds and blood viscosities not represented in the stored data are derived by interpolation.

An example of the F(BEMF)-to flow table 534 is provided as Table 2. According to this example, the BEMF-to-flow table 534 indicates that when the BEMF in the coil 132a changes at the rate of 5.5 V/s, the pump 101 impels blood at the rate of 2.5 L/min. The BEMF-to-flow table 534 may be implemented as a file, a data structure, as part of a database, or in any other suitable form.

TABLE 2

BMEF-to-Flow Map

| F(BMEF) | Blood Flow Rate (@ 10000 rpm) |
|---|---|
| 0.2 V/s | 0.75 L/min |
| 0.4 V/s | 1.5 L/min |
| 0.5 V/s | 2.0 L/min |
| 0.55 V/s | 2.4 L/min |
| 0.60 V/s | 2.5 L/min |

The data in each of the tables may be determined experimentally using the actual pump or a sample pump of similar configuration. In addition, each of the tables may be pre-loaded in the memory 520 before the pump 101 is deployed.

The instructions 540 may be instructions to be executed directly (such as machine code) or indirectly (such as scripts) by the processor. In that regard, the terms "instructions," "steps" and "programs" may be used interchangeably herein. The instructions may be stored in object code format for direct processing by the processor, or in any other computer language including scripts or collections of independent source code modules that are interpreted on demand or compiled in advance. Functions, methods and routines of the instructions are explained in more detail below. Flow estimation module 542 may include instructions for determining the blood flow rate produced by the pump 101 as further explained below, whereas pump control module 544 may include instructions for controlling the operation of the drive circuit 310 (FIG. 3) and thus controlling pump 101. The operations according to instructions 540 is further discussed below with respect to FIG. 7.

The control circuit 140 may optionally include an interface 550 which connect the control circuit 140 to an output device 560. The interface 550 may be an analog interface (e.g., audio interface) or a digital interface, such as Bluetooth. TCP/IP, 3G, and others. Where the control circuit is implemented in an implantable structure adapted to be disposed within the body of the patient, the interface 550 may include known elements for communicating signals through the skin of the patient. The output device 560, may be a speaker, a communications terminal (e.g., computer, cell phone) or any other type of device.

Although FIG. 5 functionally illustrates the processor and memory as being within the same block, it will be understood that the processor and memory may actually comprise multiple processors and memories that may or may not be stored within the same physical housing. The memory may include one or more media on which information can be stored. Preferably, the medium holding the instructions retains the instructions in non-transitory form. Some or all of the instructions and data may be stored in a location physically remote from, yet still accessible by, the processor. Similarly, the processor may actually comprise a collection of processors which may or may not operate in parallel.

Figure 7:
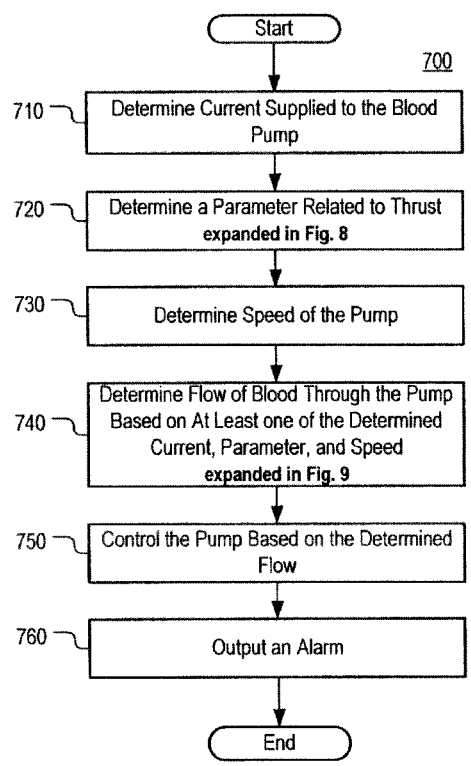
FIG. 7 depicts a flowchart of a method of operation used by the system of FIGS. 1-3.

FIG. 7 depicts a flowchart of a process 700 for determining the rate at which blood is impelled by the pump 101. At task 710, the control circuit 140 determines the amount of current that is used to power the pump 101.

Figure 8:
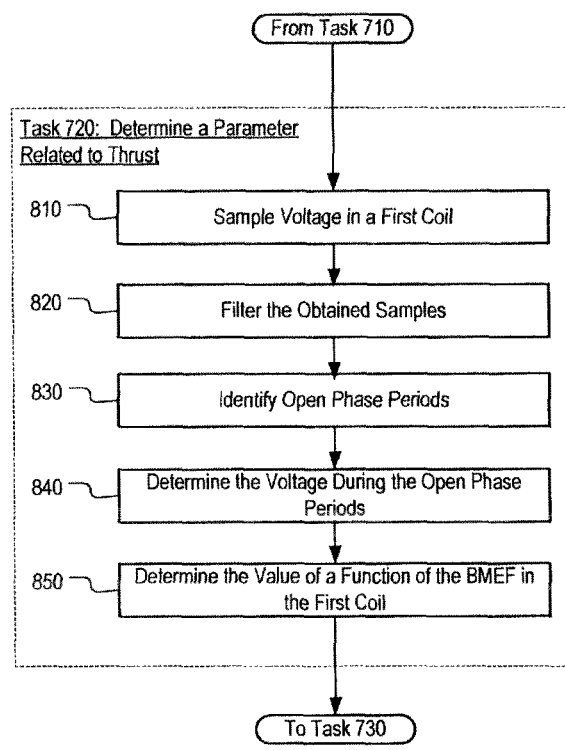
FIGS. 8 and 9 are detail flowchart depicting portions of the method FIG. 7.

At task 720, the control circuit determines a parameter related to thrust imparted on the rotor 120 by the flow of blood exiting the pump 101. In this embodiment, the determined parameter is the function F(BEMF), the rate of change of BEMF during the open phase periods of coil pair 132*a* and 132*b* as discussed above. FIG. 8 depicts the sub-steps of step 720. To determine the F(BEMF), the control circuit 140 first samples voltage across the coil pair 132*a* and 132(*b*). In one embodiment, for example, the sampling frequency may be 200 kHz (Task 810). The samples may then be filtered using an average filter. For example, the filter may be specified as Vout[i]=K*Vin[i]+ (1−K)*Vout[i−1], where 0≤K≤1 (Task 820). The control circuit 140 then identifies an open phase period. In some aspects the open-phase period based on the voltage levels of the sampled signal being under a predetermined threshold (Task 830). Once one or more open-phase periods are identified, the control circuit 140 determines the voltage across the coil 132*a* during the identified open-phase periods. The determined voltage is the BEMF (Task 840). The control circuit calculates F(BEMF), the rate of change in BEMF from the BEMF values during the open-phase periods (Task 850). The rate of change may be measured using any number of voltage samples (e.g., 2, 20, 200) taken at any sampling frequency (e.g., 200 kHz). Desirably, calculation of F(BEMF) occurs in real time.

At task 730, (FIG. 7) the control circuit 140 determines the speed of rotation of the rotor 120. As discussed above the control circuit samples voltage across the coil pair 132*a* and 132*b*, identifies open-phase periods in which the voltage appearing across the coil is less than a threshold voltage, and determines the number of the open-phase periods per unit time or, equivalently, the time between successive open-phase periods for a particular coil. The control circuit determines the speed based on this measurement. The greater the number of open-phase periods per unit time, or the lesser the time between successive open-phase periods, the faster the speed.

At task 740, the control circuit 140 determines the rate at which blood is impelled by the pump 101 based on the parameter related to thrust determined at task 720

Figure 9:
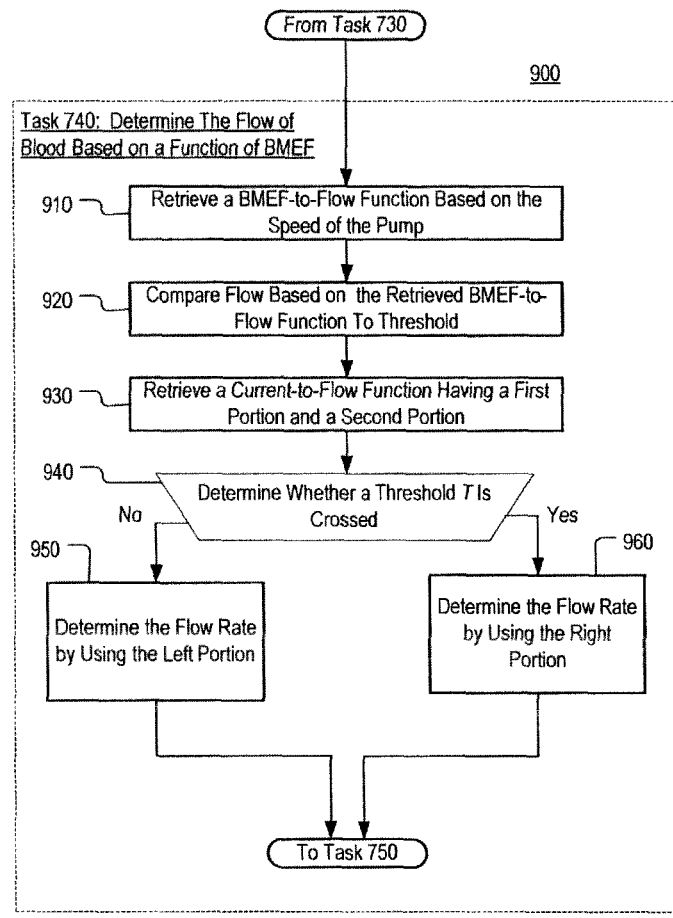

The tasks included in task 740 are shown in greater detail in FIG. 9. At task 910, the control terminal retrieves a function that maps the BEMF slope to a blood flow rate, i.e., F(BEMF)-to-flow table 534 (FIG. 5 and Table II, above), for the speed at which the pump is operating. At task 920, the control circuit 140 determines whether the blood flow rate associated with the value of F(BEMF) is above or below a predetermined threshold value T associated the function 620 (FIG. 6). As depicted in FIG. 6, the threshold value T is a value which is the same, or approximately the same, as the blood flow rate M at the fiducial point which separates the left and right regions of the current-to-flow rate relationship 610 at the speed at which the pump is operating. The control circuit may use F(BEMF)-to-flow table 534 (Table II above) and retrieve the value of flow corresponding to the value of F(BEMF). In this process, the control circuit may interpolate between stored values using standard interpolation techniques. The circuit then compares the retrieved value of flow to the threshold T. and determines whether the value of flow indicated by F(BEMF) is above or below the threshold T. In the alternative, because there is a one-to-one mapping between F(BEMF) and flow, the same step can be performed by simply comparing F(BEMF) to a threshold value of F(BEMF) indicated T' (FIG. 6) which corresponds to the threshold value of flow T. If this alternative method is used, the memory may not store the entire F(BEMF)-to-flow table 534, but instead may simply store a value T' associated with each operating speed.

At task 930, the control circuit 140 retrieves the function 610 that maps an amount of current supplied to the pump 101 to blood flow rate that is generated by the pump 101, i.e., the current-to-flow table 532 (FIG. 5 and Table 1, above).

At task 940, the control circuit 140 branches to one of two different paths. If the threshold comparison (task 920) indicates that F(BEMF) is below threshold T (FIG. 6) task 950 is executed. Otherwise, the control circuit 140 executes task 960.

At task 950, the control circuit 140 determines the rate at which blood is impelled by the pump 101 based on the left portion of the function 610. To evaluate the left portion of the function 610, the control circuit 140 may use the value of current as an index and retrieve the corresponding value of flow from the entries in the current-to-flow table 532 (and Table 1, above) that pertains to the left portion. Alternatively, the control circuit 140 may obtain two or more blood flow rate values that correspond to the same amount of current and then select the smallest one. In either process, standard interpolation techniques can be used when the value of current falls between stored values.

At task 960, the control circuit 140 determines the rate at which blood is impelled by the pump 101 based on the right portion of the function 410. To evaluate the right portion of the function 610, the control circuit 140 may use the value of current as an index and retrieve the corresponding value of flow from the entries in the current-to-flow table 532 (and Table 1, above) that pertain to the right portion. Alternatively, the control circuit 140 may obtain two or more blood flow rate values that correspond to the same amount of current and then select the largest one. In either process, standard interpolation techniques can be used when the value of current falls between stored values.

At task 750 (FIG. 7), the control circuit 740 controls the operation of the pump 101 or takes other action in response to the determined flow rate. For example, the control circuit may maintain a set point for the flow rate and a moving average of the flow rates as determined over a preset period as, for example, a few minutes. The flow rate set point may be a fixed value or a value determined on the basis of physiological parameters such as the patient's heart rate, respiratory rate or blood oxygen level. If a new value of flow rate is below the moving average by more than a predetermined amount, this may indicate either that the pump has created a suction condition at the intake, or that the outlet of the pump is blocked. For example, where the pump is drawing blood from the left ventricle, a suction condition may arise where the intake of the pump is positioned so that as the heart beats, the opening of the intake comes to rest against the wall of the ventricle and the opening is blocked. In this situation, the flow rate may fluctuate as the beating motion of the heart periodically blocks and unblocks the intake. By contrast, where the outlet of the pump is blocked, the flow rate typically will remain at a low value without such fluctuations. The control circuit can differentiate between such a suction condition and a continual blockage of the pump.

A blood pump system 1000 in accordance with yet another embodiment of the invention incorporates an active control system comprising an active control module which exerts an axial force on the rotor to counteract the effects of thrust on the rotor and maintain the rotor in a substantially constant axial position. Further examples of active control systems are provided in U.S. Published Patent Application No. 20110237863, entitled "Magnetically Levitated Blood Pump With Optimization Method Enabling Miniaturization."

Figure 10:
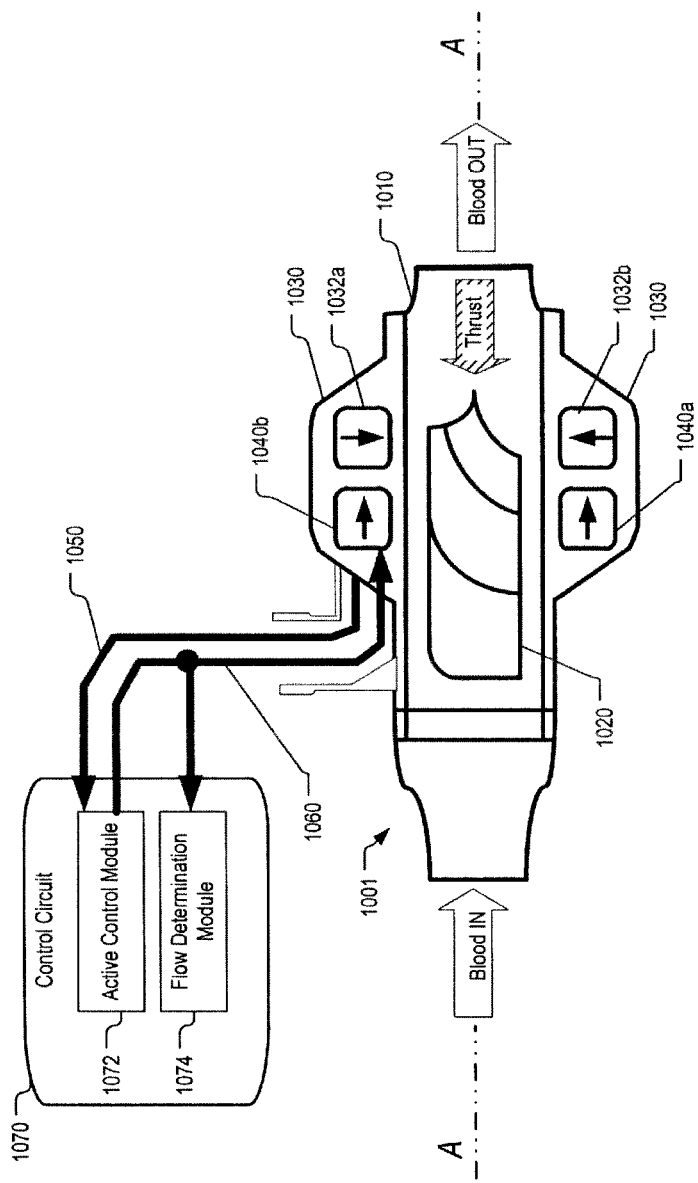
FIG. 10 is a partially, partially block diagrammatic, partial sectional view of a blood pump system in accordance with another embodiment of the invention.

System 1000 comprises a pump 1001 and control circuit 1070. The pump 1001 comprises a rotor 1020 disposed within housing 1010 and actuated by a stator 1030. The rotor 1020 comprises coils 1030. Unlike the pump 101 (FIG. 1), the pump 1001 (FIG. 10) also comprises electromagnets 1040a-b for producing a magnetic field which exerts an axial force on rotor 1020 that is opposite in direction and similar in magnitude to the thrust imparted on the rotor 1020 by the flow of blood impelled by the pump 1001. The force produced by the electromagnets balances out the thrust and allows the rotor 1020 to remain in place.

Control circuit 1070 may include an active control module 1072 and flow determination module 1070. The active control module 1072 may receive input signal(s) 1050 and outputs control signal(s) 1060. In this example, the control signal 1060 controls the magnitude of the magnetic field produced by at least one of the electromagnets 1040a-b. The control signal 1060 may be a digital directed to a controller that operates the electromagnets 1040a-b, an analog current used to power the electromagnets 1040a-b, or any other signal. Because the control signal 1060 sets the magnitude of the magnetic field of the electromagnets 1040a-b, which is used to offset the thrust imparted on the rotor 100 by the flow of blood output by the pump 101, the control signal bears a direct relationship to the thrust.

The signal 1060 constitutes another example of a parameter related to thrust and it may be used to determine blood flow rate. The flow determination module 1074 may determine the blood flow rate produced by the pump 1001 by receiving the control signal 1060 and matching it to a corresponding blood flow rate. For example, a table may be stored in a memory of the control circuit 140 that relates different values for the control signals 1040 to blood flow rate. Here again, the table may include different sets of data for different pump operating speeds and blood viscosities. The flow determination module 1074 may use the table to match the value of the control signal 1060 to a corresponding blood flow rate.

In still other arrangements, thrust can be measured directly. For example, if the pump includes a bearing which retains the rotor against axial movement, the bearing may incorporate a piezoelectric element or other force transducer. The signal from the force transducer, or a function of the signal, may be used as the parameter related to thrust.

In the embodiment discussed above with reference to FIGS. 1-9, the parameter F(BEMF) related to thrust is used to select a portion of the current-to-flow relationship 610 (FIG. 6), i.e., the left or right portion of the curve. In a variant of this approach, the system can determine flow directly from F(BEMF) using the F(BEMF)-to-flow table 534 (FIG. 5 and Table 2, above) whenever the value of flow indicated by F(BEMF) is below the threshold value T, and determine the flow based on the right portion of the current-to-flow relationship 610 when the value of flow indicated by F(BEMF) is above the threshold value T. In the particular system discussed above with reference to FIGS. 1-9, the relationship between F(BEMF) and flow is such that for values above the threshold, the slope of curve 620 becomes relatively small. In this region, a large change in flow corresponds to only a small change in F(BEMF). This makes it difficult to determine the flow accurately from F(BEMF). However, in other systems having different rotor and coil configurations, the relationship between F(BEMF) and flow provides more substantial variation of F(BEMF) per unit change in flow rate over the entire range of flow rates to be monitored. In those cases, the flow rate can be determined based solely on F(BEMF), without reference to the current used by the pump. Likewise, where another parameter related to thrust is employed, the determination of flow rate can be based solely on such other parameter. In yet another alternative, a parameter related to thrust, such as F(BEMF), can be used without use of the current-to-flow relationship even where the parameter is useful over only a limited range of flow rates. For example, using the same F(BEMF) as employed in FIGS. 1-9, the system can detect occlusion or suction events by comparing the value of F(BEMF) with a relatively low threshold, well below the threshold T' in FIG. 6. In this arrangement, F(BEMF) is used as a parameter for control or monitoring of the pump without converting it to a value of flow rate. For example, the system may be arranged simply to issue an alarm signal, or take some other predetermined action, whenever F(BEMF) falls below a threshold or remains below the threshold for a particular time. Similar strategies can be used with other parameters related to thrust. In another variant, the system can evaluate the flow rate associated with F(BEMF) and compare that value to a low threshold, below the normal operating range of flow rates.

The control circuit 140 need not more relationships between a parameter such as F(BEMF) and flow or between current and flow in the form of lookup tables as discussed above. The control circuit may retrieve and evaluate a formula that models the rate at which blood is impelled by the pump as a function of the parameter related to thrust, e.g., a formula for the function 620 (FIG. 6). Likewise, the control circuit may retrieve and evaluate a formula for the current-to-flow relationship, e.g., a formula of the function 610.

In the embodiments discussed above, the flow rate determined by the control circuit is used to control the operation of the pump. In other embodiments, the control circuit may simply determine the flow rate and send a signal representing the flow rate to an external device, and may not control operation of the pump.

Because the systems discussed above can determine flow rate through an implanted blood pump, the systems can also deduce the pressure drop across the pump. At a given viscosity and pump operating speed, there is a predetermined relationship between flow rate and pressure drop. For any given pump design, this relationship can be found by experiment and represented in tables of data. Thus, the system can calculate pressure drop from flow rate and report pressure drop in lieu of flow rate, or in addition to flow rate.

The techniques described above may be used to determine the flow rate of pumped fluids other than blood. Moreover, although the above examples are focused on axial flow pumps, the techniques discussed above can be used with other pumps where the thrust on a rotor varies with flow rate as, for example, in certain radial-flow centrifugal pumps.

Figure 11:
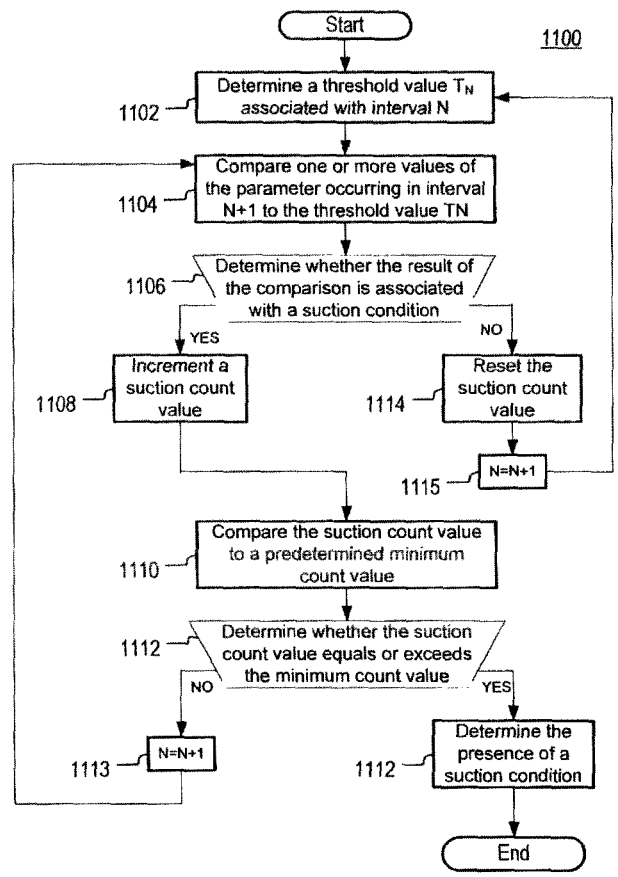
FIG. 11 depicts a flowchart of another method of operation used by the system of FIGS. 1-3.

A method of detecting a suction condition, according to one embodiment of the invention, is shown in the flow diagram 1100 of FIG. 11. At block 1102 of FIG. 11, the control circuit repeatedly evaluates a parameter at intervals N (e.g., 2 seconds long) and determines a threshold value $T_N$ associated with each interval N. The evaluated parameter may be blood flow, a function of BEMF such as BEMF itself or the first derivative of BEMF or another metric related to thrust along an axis of the rotor of the pump. The parameter may be any of the above described parameters from which the rate of blood flow in the pump may be determined. The determination of the threshold value $T_N$ may be based only on values of the parameter occurring during the interval immediately prior to the determination. Alternatively, the determination of the threshold value may be based on values of the parameter occurring during a period of time prior to the determination, including values occurring in a plurality of prior intervals (e.g., N, N−1, etc.).

During the monitored period, the waveform of the parameter may include one or more local extremes, such as local minima or local maxima representing local minima in the flow through the pump. If the parameter is directly related to flow, local minima will represent the local minima in the flow, whereas if the parameter is inversely related to flow, local maxima will represent local minima in the flow. The threshold value may be based on the one or more minima or maxima of the waveform during the monitored period. For example, the threshold value may be based on a selected value related to the minimum or maximum during the monitored period, such as an absolute minimum, an absolute maximum, a mean, median or mode of the maxima or minima, or any combination of the above. Further, the threshold value may have a predetermined relation to the selected value. For example, the threshold may be a predetermined percentage above or below the selected value, or may be offset from the selected value by a predetermined amount.

At block 1104, the control circuit compares one or more selected values of the parameter occurring in the next interval N+1 to the threshold value from the previous determination $T_N$. At blocks 1106-1112, the control circuit determines the presence or absence of a suction condition based at least in part on the result of the comparison at block 1104. At block 1106, the control circuit determines whether the result of the comparison at block 1104 is associated with a suction condition. For example, if the monitored parameter is the BEMF of the coils or another parameter directly related to flow, such as the first derivative of BEMF, the value of the parameter at interval N+1 being less than $T_N$ indicates a result associated with the presence of a suction condition. Alternatively, if the parameter is inverse to flow, the value of the parameter at interval N+1 exceeding $T_N$ indicates a result associated with the presence of a suction condition. If the control circuit determines that the result of the comparison is associated with a suction condition, then the control circuit proceeds to block 1108, and increments a suction count value. At block 1110, the control circuit compares the suction count value to a predetermined minimum count value. At block 1112, if the suction count value equals or exceeds the minimum count value, then the control circuit determines the presence of a suction condition.

If the suction count value does not equal or exceed the minimum count value, the control circuit increments N at block 1113, and then loops back to block 1104. At block 1104, the control circuit initiates the comparison of the value of the parameter occurring in a new interval with the previously established threshold value $T_N$. Stated another way, if the result of the comparison for an interval is associated with a suction condition, the control circuit does not use the parameter values measured during that interval to update the threshold. Thus, so long as the new values continue to be associated with the suction condition, new values are compared to the threshold value established based on values which did not indicate a suction condition.

Returning to block 1106, if the control circuit determines that the result of the comparison is not associated with a suction condition, then the suction count value is not incremented, and the control circuit proceeds to block 1114, where the suction count value is reset to its starting value, typically zero. In this embodiment, the suction count value effectively indicates the number of consecutive intervals for which the result of the comparison is associated with a suction condition.

During normal operation of the pump, with no values indicative of a suction condition, the suction count value is reset and the control circuit proceeds to block 1115, where N is incremented to N+1 and returns to block 1102. At block 1102, the values from interval N+1 are used to recalculate the threshold value $T_N$, and the recalculated threshold value is used from the next comparison with values of the parameter measured during interval N+2. Stated another way, while the pump is operating normally, with no measured values indicative of a suction condition, the control circuit repeatedly recalculates the threshold value. This repeated recalculation assures that the control circuit will not determine the existence of a suction condition if the flow through the pump declines due to a partial or total occlusion. An occlusion normally arises due to a gradual accumulation of thrombus or other material within the pump or within an inlet or outlet cannula associated with the pump. During such gradual accumulation, the threshold value will progressively decline, so that the measured values from new intervals will remain above the threshold value. As further discussed below, the control circuit may use other routines to determine the existence of an occlusion.

Figure 12:
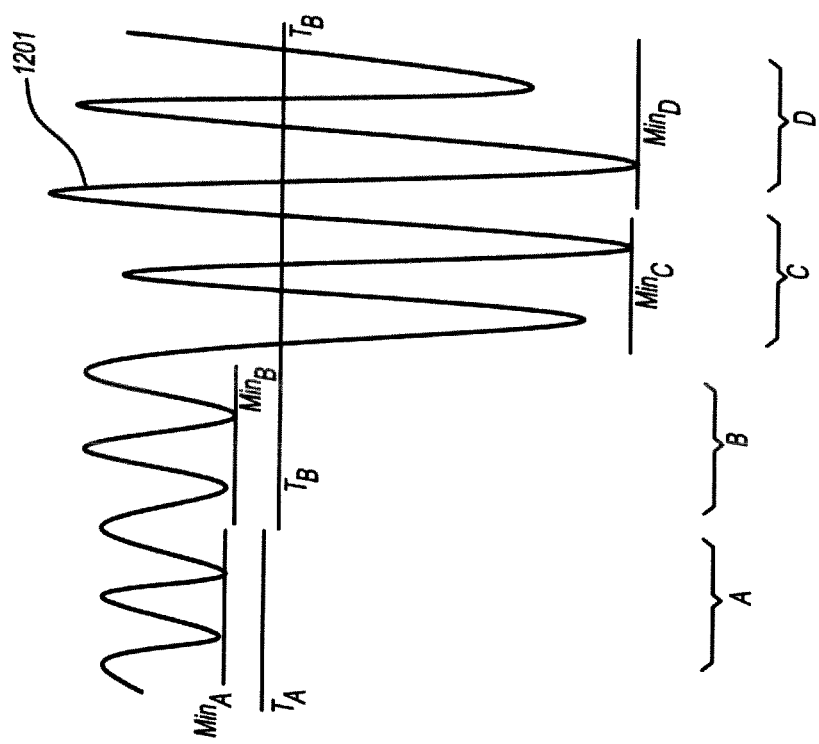
FIG. 12 is graph depicting an embodiment of the method depicted in FIG. 11.

FIG. 12 illustrates one example of the suction condition determination based on a parameter using the routine of FIG. 11. In FIG. 12, the parameter, such as BEMF, is characterized by a waveform 1201. The waveform shows the fluctuation in flow associated with the cardiac cycle of the patient's heart during several intervals A-D. During each heartbeat, a local minimum occurs during ventricular diastole. The length of each interval is selected so that one or more instances of ventricular diastole, and hence one or more local minima, occur during each interval. Stated another way, the duration of each interval is selected to equal or exceed the longest anticipated period of the patient's heartbeat. At interval A, a threshold value $T_A$ is determined based on an absolute minimum value $MIN_A$ of the waveform during interval A. In the example of FIG. 12, threshold value $T_A$ is 1% lower than $MIN_A$. Next, at interval B, the previously determined threshold value $T_A$ is compared to an absolute minimum value $MIN_B$ of the waveform during interval B. Because $MIN_B$ is greater than $T_A$, the result of the comparison is not associated with a suction condition. The threshold value is thus updated from $T_A$ to $T_B$, which is 1% lower than $MIN_B$.

Next, at interval C, the previously determined threshold value $T_B$ is compared to an absolute minimum value $MIN_C$ of the waveform during interval C. Because $MIN_C$ is not greater than $T_B$, the result of the comparison is associated with a suction condition. The suction value count is thus incremented, and the threshold value $T_B$ is not updated. At interval D, the threshold value $T_B$ is again compared to an absolute minimum value $MIN_D$ of the waveform during interval D. Because $MIN_D$ is not greater than $T_B$, the result of the comparison is again associated with a suction condition. The suction value count is thus again incremented, and the threshold value $T_B$ is again not updated. For purposes of example, if the minimum count value is set to two, the suction count value would equal the minimum count value, and the control circuit would determine the presence of a suction condition. In other examples, the minimum count value may be set higher than two (e.g., 5).

Where a suction condition is found, the control circuit may command the drive circuit to momentarily reduce the speed of the pump so as to help clear the condition. If the momentary reduction in pump speed does not cure the low flow rate, the control circuit may issue an alarm signal (task 760, FIG. 7) through the interface 550 (FIG. 5) to output device 560, so that the patient or a caregiver is notified of the problem.

If the flow rate increases responsive to the momentary reduction in speed, the control circuit may command the drive circuit to increase the speed of the pump. Preferably, the speed of the pump is increased back to the speed used prior to the momentary reduction. The increase may be more gradual than the rate of the reduction. If the suction condition resumes upon increasing the speed of the pump, the control circuit may command the drive circuit to repeat the momentary reduction of the pump speed so as to reattempt to clear the suction condition. Repeating the reduction of pump speed may involve reducing the pump speed to a lower speed than the initial reduction. In some examples, the pump speed may first be reduced by 15%, and may subsequently be reduced by 25%. Reducing the pump speed to varying speeds is desirable in order to achieve a balance between effectiveness at clearing the condition and maintaining the patient's blood circulation. For example, in some situations the smaller reduction (e.g., 15%) may be sufficient to clear the condition and may maintain greater blood perfusion compared to the greater reduction (e.g., 25%). Alternatively, in other situations, the smaller reduction may be insufficient to clear the condition, in which case the larger reduction may be necessary despite the loss of perfusion.

As with the first momentary reduction in speed, if the flow rate increases responsive to the second momentary reduction, the control circuit may command the drive circuit to gradually increase the speed of the pump. If the suction condition resumes upon increasing the speed of the pump, the control circuit may command the drive circuit to initiate another momentary reduction of the pump speed so as to reattempt to clear the condition. In some examples, the drive circuit may cycle between reducing the pump to the smaller reduced speed and the greater reduced speed.

The drive circuit is not limited to lowering the speed of the pump to one of only two reduced speeds. In other examples, the speed of the pump may be lowered to three or more reduced speeds. Additionally, the drive circuit may control the speed of the pump such that the pump cycles among the reduction speeds (e.g., 1, 2, 3, 1, 2, 3, etc.) until the condition is cleared.

Figure 13:
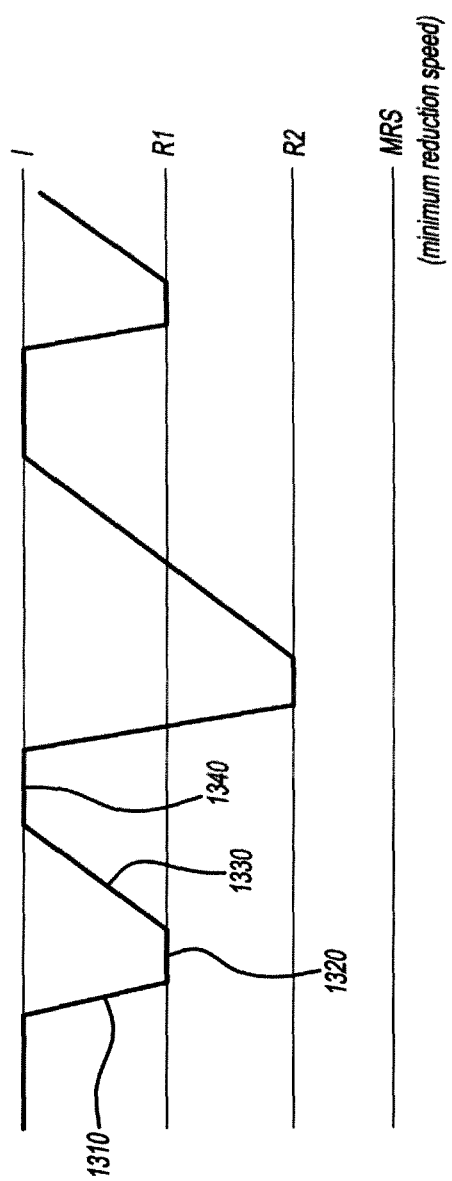
FIG. 13 is a graph depicting a method of operation used by the system of FIGS. 1-3.

One example of foregoing methods of controlling the pump speed in order to clear a suction condition is shown in greater detail in FIG. 13. As depicted in FIG. 13, the pump may operate at an initial speed I. Upon detection of a suction condition, the drive circuit reduces the pump speed (1310) to a first reduced speed R1, at which the pump operates temporarily (1320). The drive circuit then gradually increases the pump speed (1330) to the initial speed I, at which the pump continues to operate (1340). In some examples, where the pump is a continuous rotary blood pump such as that shown in FIG. 1, and where the initial speed I is on the order of 14,000-20,000 revolutions per minute (RPM), the pump speed may be increased at a rate of 100 RPM per second. During the increase and subsequent operation, the control circuit may verify whether the suction condition resumes. If the suction condition resumes, the drive circuit may repeat the same steps as above, except that the pump speed is reduced to a second reduced speed R2 that is lower than the first reduced speed. In the example of FIG. 13, this process repeats itself until the suction condition is cleared upon lowering the pump and does not resume upon increasing the pump speed to the initial speed. The control circuit may keep a count of repetitions. If the count reaches a predetermined maximum, the control circuit may issue an alarm signal.

The reduced speeds may be limited by a minimum reduction speed (MRS) value. For example, the control circuit may be programmed such that the reduced speed is never set lower than minimum reduction speed value. In FIG. 13, a minimum reduction speed value of 12,000 revolutions per minute (RPM) is set. Thus, neither the first reduced speed nor the second reduced speed may be set below 12,000 RPM. Thus, if the initial speed I is close the minimum reduction speed MRS, the control circuit will reduce the pump speed to MRS on each repetition.

Figure 14:
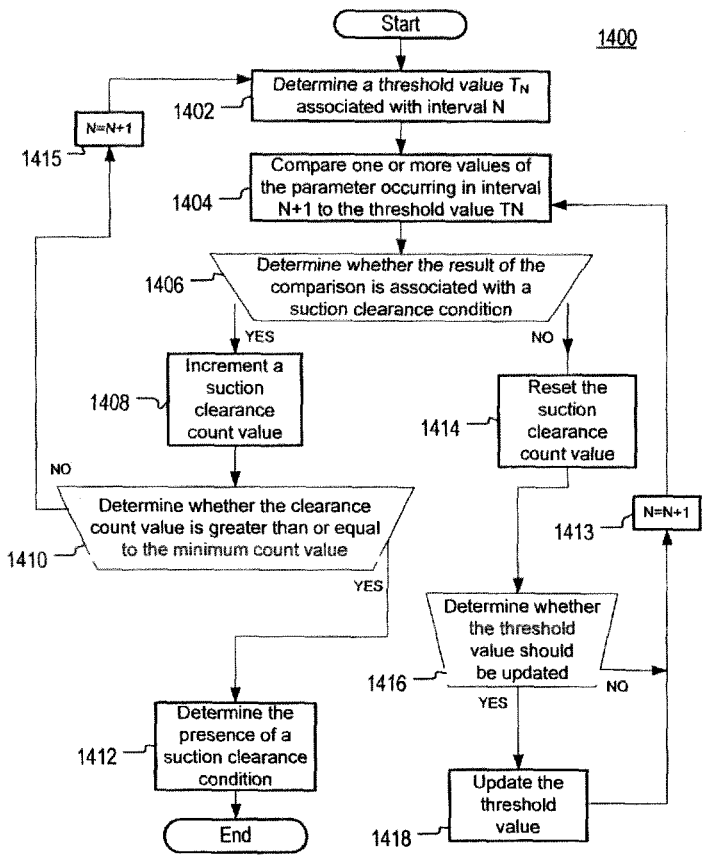
FIG. 14 depicts a flowchart of another method of operation used by the system of FIGS. 1-3.

Clearance of a suction condition may be detected using a method similar to the method for detecting a suction condition. For example, the flow diagram 1400 of FIG. 14 illustrates one method for detecting a suction clearance condition. In FIG. 14, blocks 1402-1114 generally correspond to the steps described in connection with blocks 1102-1114 of the flow diagram 1100 of FIG. 11, with certain differences. However, the method shown in FIG. 14 is initiated when the system is in a suction condition. Thus, this routine may begin after the method of FIGS. 11 and 12 has determined that a suction condition exists. Firstly, in block 1406, instead of determining whether the result of the comparison is associated with a suction condition, the control circuit determines whether the result of the comparison is associated with a suction clearance condition, i.e., an increase in the local minimum flow through the pump vis-à-vis a local minimum flow encountered during the suction condition. In some examples (such as if the monitored parameter is the BEMF of the coils), the value of the parameter at interval N+1 being greater than $T_N$ indicates a result associated with the presence of a suction clearance condition. In other examples (such as if the parameter is derived from the inverse of BEMF), the value of the parameter at interval N+1 being less than $T_N$ indicates a result associated with the presence of a suction clearance condition. Stated another way, a value which indicates an appreciable increase in flow above the threshold value is indicative of a suction clearance condition.

If the comparison indicates a suction clearance condition, the control circuit proceeds to block 1408. In block 1408, instead of incrementing a suction count value, the control circuit increments a clearance count value associated with how long the suction condition has been cleared. The clearance count value is then compared to a clear minimum count value at block 1410 in order to determine at block 1412 whether the suction condition has been cleared. If the count value equals or exceeds the minimum, this indicates that the flow has remained appreciably above the threshold $T_N$ for an appreciable amount of time, and the control circuit thus determines that the suction condition has been cleared. If the count does not equal or exceed the minimum, the control circuit proceeds to block 1413, where N is incremented, and returns to block 1404, where the comparison repeats using the values for the next interval and the previously determined threshold, without updating.

If the comparison at block 1408 yields a result that is not indicative of a suction clearance value, the control circuit proceeds to block 1414, where it resets the clearance count value to its starting value, typically zero. Then, at block 1416, the control circuit computes a new threshold value $T_{N+1}$ based on the parameter values measured in the current interval, and compares that value $T_{N+1}$ to the previously-established threshold value (e.g., $T_N$).

At block 1416 the control circuit determines whether the threshold value should be updated by comparing the threshold value of the present interval $T_{N+1}$ to the previously-established threshold value. The threshold value is updated to $T_{N+1}$ only if $T_{N+1}$ represents a lower flow than the previously established threshold value. Thus, if the threshold value is based on a parameter such as BEMF which varies directly with flow, and the presently determined threshold value $T_{N+1}$ is greater than the previously established threshold value, the threshold value is not updated. If the presently determined threshold value $T_{N+1}$ is not greater than the previously established threshold value, the threshold value is updated. In an example where the monitored parameter is inverse to the flow, such as the inverse of the BEMF of the coils, the threshold value may be updated under the opposite circumstances (i.e., when the presently determined threshold value is not less than the previously determined threshold value). Thus, while the suction clearance condition persists, the control circuit selects a suction clearance threshold based on the lowest flow measured during the suction condition and determines that the suction has been cleared when the flow rises substantially above that threshold value.

FIG. 15 illustrates one embodiment of a suction clearance determination using the routine of FIG. 14. In FIG. 15, the parameter is characterized by a waveform 1501. At the beginning of the waveform, the system is in a suction condition. At interval A, a threshold value $T_A$ is determined based on an absolute minimum value $MIN_A$ of the waveform during interval A. In the example of FIG. 12, threshold value $T_A$ is 50% higher than $MIN_A$. During interval B, the previously determined threshold value $T_A$ is compared to an absolute minimum value $MIN_B$ of the waveform during interval B. Because $MIN_B$ is less than $T_A$, the result of the comparison is not associated with a suction clearance condition. The control circuit resets the suction clearance counter to its starting value (step 1414, FIG. 14). Because $T_B$ is less than $T_A$, indicating that the minimum flow during interval B is lower than the minimum flow during interval A, the threshold value is updated from $T_A$ to $T_B$, which is 50% higher than $MIN_B$ and thus lower than $T_A$. (steps 1416 and 1428). Next, at interval C, the previously determined threshold value $T_B$ is compared to an absolute minimum value $MIN_C$ of the waveform during interval C. Because $MIN_C$ is less than $T_B$, the result of the comparison is not associated with a suction clearance condition. Thus, the system again resets the suction clearance count to its starting value. However, because a threshold $T_C$ computed from $MIN_C$ is greater than $T_B$, the threshold value is not updated and remains $T_B$.

At interval D, the previously determined threshold value $T_B$ is compared to an absolute minimum value $MIN_D$ of the waveform during interval D. Because $MIN_D$ is greater than $T_B$, the result of the comparison is associated with a suction clearance condition. The clearance count value is thus incremented, and the threshold value $T_B$ is not updated. At interval E, the threshold value $T_B$ is compared to an absolute minimum value $MIN_E$ of the waveform during interval E. Because $MIN_E$ is not less than $T_B$, the result of the comparison is again associated with a suction clearance condition. The clearance count value is thus again incremented, and the threshold value $T_B$ is again not updated. For purposes of example, if the minimum clearance count value Is set to two, the clearance value count would equal the minimum count value, and the control circuit would determine the presence of a suction clearance condition. In other examples, the minimum clearance count value may be set higher than two (e.g., 10).

Also, if a flow reduction indicates a blockage or occlusion, the control circuit may issue the same alarm signal or a different alarm signal. Unlike the suction condition, which may result in sudden drop of the flow rate of blood without significantly affecting the average flow rate of blood, a blockage results in a significant drop of the average flow rate. Thus, the control circuit can detect a blockage based on a drop in the average flow rate of blood. For example, the control circuit may compare an average of the flow rate, or a parameter related to flow rate calculation over a period longer than a heartbeat (e.g., a few seconds, a few minutes, etc.) against a preset minimum flow value. If this comparison indicates a low flow, but a suction condition does not exist, the control circuit determines that an occlusion condition exists. The control circuit only determines that an occlusion condition exists when a suction condition does not also exist since in some situations the drop in average flow of blood may be due to the suction condition. Also, unlike the suction condition, which is treated by reducing the speed of the pump, the blockage may be treated by raising the speed of the pump. For example, if it is determined that the moving average flow rate of blood is below the set point, the control circuit 140 may increase the speed of the pump 101. If the blood flow rate is above the set point, the control circuit 101 may reduce the pump speed.

FIGS. 7-9 and 11-15 are provided as examples. At least some of the tasks associated with FIGS. 7-9 and 11-15 may be performed in a different order than represented, performed concurrently or altogether omitted.

In the embodiment discussed above in connection with FIGS. 6-9, computation of flow rate is based on a particular function of BEMF, namely the rate of change or slope of the BEMF during open phase periods. However, other functions of BEMF may be used. For example, the function of BEMF may be simply the magnitude of BEMF detected. Stated another way, as used in this disclosure the expression "function of BEMF" includes BEMF itself as well as other functions of BEMF. Use of a function of BEMF as a parameter for flow rate determination is particularly advantageous because it is not necessary to incorporate any additional transducer into the pump. In effect, the coils of the pump act as the transducer to measure BEMF and thus measuring displacement of the rotor and, indirectly, measuring thrust on the rotor.

In the embodiment discussed above in connection with FIGS. 11-15, it is not essential to compute flow rate. The detection of a suction condition and/or suction clearance condition may be accomplished using the BEMF or a function of the BEMF directly. Typically, a suction condition only occurs when the blood flow rate slows and drops below the threshold T depicted in FIG. 6. Therefore, the control circuit may focus exclusively on the F(BEMF) values in the left region of FIG. 6 while determining the presence of a suction condition. In a simplified embodiment, the F(BEMF)-to-flow table 534 in the memory, and the structures used to store a current-to-flow table 532 in the memory, can be omitted.

Other parameters related to thrust on the rotor may be employed instead of a function of BEMF. For example, where the pump is equipped with a transducer other than the coils which can directly measure the axial position of the rotor, control circuit 140 may determine the flow rate based in whole or in part on a signal from the transducer which represents displacement. Stated another way, the displacement is a parameter related to thrust on the rotor. Any other parameter related to thrust on the rotor can be used.

As these and other variations and combinations of the features discussed above can be utilized without departing from the subject matter as defined by the claims, the foregoing description of exemplary aspects should be taken by way of illustration rather than by way of limitation of the subject matter as defined by the claims. It will also be understood that the provision of the examples described herein (as well as clauses phrased as "such as," "e.g.," "including" and the like) should not be interpreted as limiting the claimed subject matter to the specific examples; rather, the examples are intended to illustrate only some of many possible aspects.

The invention claimed is:

1. A control circuit for monitoring the operation of an implantable blood pump, the control circuit comprising:
    a threshold value determination circuit operative to repeatedly determine a threshold value of a parameter related to thrust along an axis of a rotor of the pump based on values of the parameter occurring during a period of time prior to each determination;
    a comparison circuit operative to compare one or more values of the parameter with the threshold value from the last previous determination; and
    a condition determination circuit operative to determine the presence or absence of one of a suction condition and a suction clearance condition based at least in part on the result yielded by the comparison circuit.

2. A control circuit as in claim 1, wherein, the condition determination circuit is operative to:
    increment a suction count value each time the comparison circuit yields a result associated with a suction condition; and
    determine the presence or absence of a suction condition only if the suction count value reaches a predetermined minimum count value.

3. A control circuit as in claim 1, wherein, the condition determination circuit is operative to:
    increment a clearance count value each time the comparison circuit yields a result associated with a suction clearance condition; and
    determine the presence or absence of a suction clearance condition only if the clearance count value reaches a predetermined minimum count value.

4. A control circuit as in claim 1, wherein the threshold value determination circuit is operative to determine the threshold value based on at least one of a minimum, maximum, mean, median, and mode of the local extremes of the parameter occurring during the period of time prior to the threshold value determination.

5. A control circuit as in claim 4, wherein the threshold value is a predetermined percentage below or above said at least one of a minimum, maximum, mean, median, and mode of the local extremes of the parameter.

6. A control circuit as in claim 1, wherein the threshold value determination circuit is operative to continue repeatedly determining the threshold value only if the comparison circuit yields a result not associated with one of the suction condition and the suction clearance condition.

7. A control circuit as in claim 1, wherein, in determining the presence or absence of a suction clearance condition, the threshold value determination circuit is operative to update a previously determined threshold value with a presently determined threshold value only if the presently determined threshold value is lower than the previously determined threshold value.

8. A control circuit as in claim 1, further comprising a drive circuit operative to:
    in response to the condition determination circuit detecting a suction condition, reduce the speed of the pump from a starting speed to a reduced speed; and
    gradually increase the speed of the pump from the reduced speed to the starting speed, wherein the condition determination circuit is further operative to determine the presence or absence of a suction condition based at least in part on a comparison of the threshold value and one or more values of the parameter occurring during a period of time subsequent to the drive circuit increasing the pump speed.

9. An implantable blood pump system comprising:
    a pump including a housing having an axis, and a rotor disposed within the housing, the rotor being rotatable around the axis; and
    the control circuit of claim 1, wherein the control circuit is operatively coupled to the pump.

10. An implantable blood pump system as in claim 9, wherein the pump includes a stator operatively coupled to the control circuit, the stator incorporating a plurality of coils for applying a rotating magnetic field to the rotor, wherein the parameter is based on back electromotive force (BEMF) in one or more of the plurality of coils.

11. A control circuit for monitoring the operation of an implantable blood pump operatively coupled to the control circuit, the control circuit operative to determine the presence and clearance of a suction condition and further comprising a drive circuit operative to:
  in response to the control circuit determining a suction condition exists, reduce the speed of the pump from a starting speed to one of a first and second reduced speed, the first reduced speed being faster than the second reduced speed; then
  increase the speed of the pump from said reduced speed to the starting speed, the rate of increasing the speed of the pump being more gradual than the rate of reducing the speed of the pump;
  wherein the drive circuit is operative to repeat the reducing and increasing steps only until the control circuit determines the suction condition is cleared, and wherein the repeated reduction of the pump speed alternates between the first and second reduced speeds.

12. A control circuit as in claim 11, wherein the drive circuit is operative to increase the speed of the pump only in response to a determination that a suction condition is cleared.

13. A control circuit as in claim 12, wherein the control circuit is operative to determine the clearance of the suction condition both after the drive circuit reduces the speed of the pump and again after the drive circuit increases the speed of the pump.

14. An implantable blood pump system comprising:
  a pump including a housing having an axis, and a rotor disposed within the housing, the rotor being rotatable around the axis; and
  the control circuit of claim 11, wherein the control circuit is operatively coupled to the pump.

15. An implantable blood pump system as in claim 14, wherein the pump includes a stator operatively coupled to the control circuit, the stator incorporating a plurality of coils for applying a rotating magnetic field to the rotor, wherein each of the first and second reduced speeds is 12,000 RPM or faster.

16. A control circuit as in claim 11, wherein the drive circuit is further operative to:
  reduce the speed of the pump to a third reduced speed, the first and second reduced speeds each being faster than the third reduced speed;
  increase the speed of the pump from the third speed to the starting speed, the rate of increasing the speed of the pump being more gradual than the rate of reducing the speed of the pump;
  wherein the repeated reduction of the pump speed cyclically alternates among the first, second, and third reduced speeds.

17. An implantable blood pump system comprising:
  a pump including a housing having an axis, and a rotor disposed within the housing, the rotor being rotatable around the axis, wherein the pump includes a stator operatively coupled to the control circuit, the stator incorporating a plurality of coils for applying a rotating magnetic field to the rotor; and
  a control circuit operatively coupled to the pump and configured to:
  determine a threshold value based directly on a measured back electromotive force (BEMF) in one or more of the plurality of coils; and
  determine the presence or absence of a suction condition based at least in part on the threshold value.

18. An implantable blood pump system as in claim 17, wherein the threshold value is a predetermined percentage below or above the measured BEMF.

19. A method for monitoring operation of an implantable blood pump, the method comprising:
  repeatedly determining a threshold value of a parameter related to thrust along an axis of a rotor of the pump based on values of the parameter occurring during a period of time prior to each determination;
  comparing one or more values of the parameter with the threshold value from the last previous determination; and
  determining the presence or absence of one of a suction condition and a suction clearance condition based at least in part on the comparison.

20. A method as in claim 19, wherein the step of determining the presence or absence of a suction condition includes incrementing a suction count value each time the comparison yields a result associated with a suction condition, and determining the presence or absence of a suction condition only if the suction count value reaches a predetermined minimum count value after a predetermined number of values have been compared with the threshold values.

21. A method as in claim 19, wherein the step of determining the presence or absence of a suction clearance condition includes incrementing a clearance count value each time the comparison yields a result associated with a suction clearance condition, and determining the presence or absence of a suction clearance condition only if the clearance count value reaches a predetermined minimum count value after a predetermined number of values have been compared with the threshold values.

22. A method as in claim 19, further comprising:
  reducing the speed of the pump from a starling speed to a reduced speed;
  gradually increasing the speed of the pump from the reduced speed to the starting speed; and
  determining the presence or absence of a suction condition based at least in part on a comparison of the threshold value and one or more values of the parameter occurring during a period of time subsequent to increasing the pump speed.

23. A method of detecting a suction condition in a ventricular assist pump comprising the steps of:
  (a) monitoring a parameter related to flow through the pump;
  (b) detecting local extreme values of the parameter representing minimum blood flow through the pump occurring during ventricular diastole;
  (c) comparing the local extreme value representing a local minimum in blood flow through the pump during a later ventricular diastole with the local extreme value representing a local minimum in blood flow through the pump during an earlier ventricular diastole and determining a change in the local extreme values based on such comparison; and
  (d) comparing the change to a standard and determining the presence or absence of a suction condition based on the comparison.

24. The method of claim 23, wherein comparing the change to a standard comprises the steps of:
  incrementing a suction count value each time the comparison yields a result associated with a suction condition; and
  determining the presence or absence of a suction condition only if the suction count value reaches a predetermined minimum count value.

25. An implantable blood pump system comprising:
a ventricular assist pump including a housing having an axis, and a rotor disposed within the housing, the rotor being rotatable around the axis; and
a control circuit operatively coupled to the pump, wherein the control circuit is configured to detect a suction condition in the pump using the method of claim 23.

26. A method of detecting clearance of a suction condition in a ventricular assist pump comprising the steps of:
(a) monitoring a parameter related to flow through the pump;
(b) detecting local extreme values of the parameter representing minimum blood flow through the pump occurring during ventricular diastole;
(c) comparing the local extreme value representing a local minimum in blood flow through the pump during a later ventricular diastole with the local extreme value representing a local minimum in blood flow through the pump during an earlier ventricular diastole and determining a change in the local extreme values based on such comparison; and
(d) comparing the change to a standard and determining the clearance or persistence of a suction condition based on the comparison.

27. The method of claim 26, wherein the local extreme value representing a local minimum in blood flow through the pump during an earlier ventricular diastole represents the lowest minimum in blood flow through the pump occurring between an onset of the suction condition and the later ventricular diastole.

28. An implantable blood pump system comprising:
a ventricular assist pump including a housing having an axis, and a rotor disposed within the housing, the rotor being rotatable around the axis; and
a control circuit operatively coupled to the pump, wherein the control circuit is configured to detect clearance of a suction condition in the pump using the method of claim 26.

* * * * *